United States Patent [19]

Fournier

[11] Patent Number: 5,461,476
[45] Date of Patent: Oct. 24, 1995

[54] OPTICAL APPARATUS FOR RECEIVING SCATTERED LIGHT

[75] Inventor: Georges R. Fournier, Holland, Canada

[73] Assignee: Department of National Defense of Canada, Ottawa, Canada

[21] Appl. No.: 349,464

[22] Filed: Dec. 5, 1994

Related U.S. Application Data

[63] Continuation of Ser. No. 57,477, May 3, 1993, abandoned.

[30] Foreign Application Priority Data

Nov. 30, 1992 [CA] Canada ................................ 2084152

[51] Int. Cl.[6] ............................. G01N 21/00; H01J 5/16
[52] U.S. Cl. ................... 356/343; 250/574; 250/227.28; 385/115
[58] Field of Search ..................... 356/335–343; 250/574, 575, 227.11, 222.2, 227.28, 227.25; 385/115, 116, 120, 121, 114

[56] References Cited

U.S. PATENT DOCUMENTS

| | | | |
|---|---|---|---|
| 3,310,680 | 3/1967 | Hasegawa | 356/343 |
| 3,835,315 | 9/1974 | Gravitt, Jr. | 250/574 |
| 4,188,121 | 2/1980 | Hirleman et al. | 356/343 |
| 4,779,003 | 10/1988 | Tatsuno | 356/336 |
| 4,882,478 | 11/1989 | Hayashi et al. | 356/343 |
| 4,914,310 | 4/1990 | Jarofski | 356/343 |
| 4,978,850 | 12/1990 | Nakamura et al. | 250/227.11 |

FOREIGN PATENT DOCUMENTS

| | | | |
|---|---|---|---|
| 0160741 | 9/1984 | Japan | 356/335 |
| 0100637 | 5/1987 | Japan | 356/335 |

*Primary Examiner*—Hoa Q. Pham
*Attorney, Agent, or Firm*—David P. Gordon

[57] ABSTRACT

Optical apparatus having an optical fiber to receive light incident thereon at one end, and a detector located adjacent the other end of the optical fiber to receive light passing through the optical fiber and emitting from the other end thereof to be incident on the detector for analysis purposes.

2 Claims, 1 Drawing Sheet

5,461,476

OPTICAL APPARATUS FOR RECEIVING SCATTERED LIGHT

This application is a continuation of application Ser. No. 08/057,477 filed May 3, 1993 now abandoned.

FIELD OF THE INVENTION

This invention relates to optical apparatus and particularly to optical apparatus for receiving scattered light.

BACKGROUND OF THE INVENTION

Transmissometers and scattering meters need to measure light at very low levels with reliability and reproducibility. Parasitic light, produced by scattering off optical surfaces or the dust on them, must be kept to a minimum and must not change with time in order that its effect may be subtracted accurately from the received signal. Unfortunately, the collecting optics for such apparatus are complex and generally involve many optical surfaces which are difficult to clean and align. This results in a large parasitic signal.

Standard optics, because of their rigid geometric disposition requirements, take up a lot of space which forces the overall device to be larger. This is merely annoying in an instrument designed for the laboratory. However, for an instrument designed to perform measurements in the field, too large a size may completely preclude or at best severely curtail its use.

In order to improve the situation, apparatus has previously been designed wherein the received beam is separated into several beams by a set of beam-splitters arranged in series. At the focus of each beam an optical mask is inserted. The optical mask for the direct transmission channel has a hole of small diameter at its center. The various scattered channels have rings cut out of them. The outer and inner diameters of the rings define the acceptance angles for the scattered light. The angles θ are related to the diameters D by the following formula:

$$\theta = \frac{D}{2F}$$

where F is the focal length of the primary lens of the receiver. The light transmitted by each mask is then collected onto the detectors by short focal length lenses situated behind each mask. The lenses are disposed in such a way as to image the total entrance plane of the primary lens on the detectors.

In another prior art method, a special detector assembly is fabricated. This assembly consists of a set of ring detectors and a central circular detector. In this case, the angles of acceptance are related to the various inner and outer diameters of the detectors by the formula given above. The primary focusing lens and the face of the detector assembly are the only optical surfaces present in this method.

It has become apparent that the disadvantage of the first-mentioned prior art method is the large number of optical elements that have to be aligned precisely and then maintained in position rigidly even when the transmissometer-nephelometer is moved or bumped hard, as it will be in field use. The surfaces of these optical elements have to be cleaned carefully before any alignment and elaborate precautions have to be taken to ensure that they remain clean during and after the alignment. This is essential since the scattering of these surfaces will be seen by the instrument and will considerably reduce its sensitivity and accuracy. For these reasons, maintenance of such a system is a complex undertaking.

In the second prior art method mentioned above, the limitations are principally due to electronic problems. The optics are simple in this apparatus and involve only the primary focusing lens and the detector assembly. The first problem of an electronic nature is due to cross-talk between the various detectors. This means that some portion of the signal falling on a given detector will be seen by the others. Since the detectors of scattered light receive, in general, signals which are much smaller than the transmitted signal in the central detector of the array, they will be swamped by the induced cross-talk and their readings will be inaccurate. The second problem of an electronic nature is due to the noise inherent in the detectors. In forward-angle scattering the signal gets much weaker as the angle is increased and one would therefore like to collect it over as large an area as possible. However, if one increases the area of the detector the electronic noise increases as the square root of the area. The capacitances of the detector also increases as the area of the detector increases and this further increases the noise of the transimpedance amplifiers connected to them. The accuracy of the device is therefore severely compromised. This complication is avoided in the first prior art apparatus mentioned above but at the expense of using separate lenses to reduce the image of each ring with various magnifications onto detectors of the same size.

It is an object of the present invention to provide optical apparatus in which the above-mentioned disadvantages are reduced or substantially obviated.

SUMMARY OF THE INVENTION

According to the present invention there is provided optical apparatus including an optical fiber to receive light incident thereon at one end, and a detector located adjacent the other end of said optical fiber to receive light passing through said optical fiber and emitting from the other end thereof to be incident on said detector for analysis purposes.

According to one embodiment of the invention there is provided optical apparatus including a plurality of fibers, a plurality of detectors, said fibers being arranged in groups, and a respective detector being responsive to each group to provide an indication of the light from the respective group. The groups may comprise rings of optical fibers and each ring of optical fibers may be separated from the next by an absorbing spacer.

BRIEF DESCRIPTION OF THE DRAWINGS

An embodiment of the present invention will now be described, by way of example, with reference to the accompanying drawings in which.

DESCRIPTION OF THE PREFERRED EMBODIMENT

Figure 1:
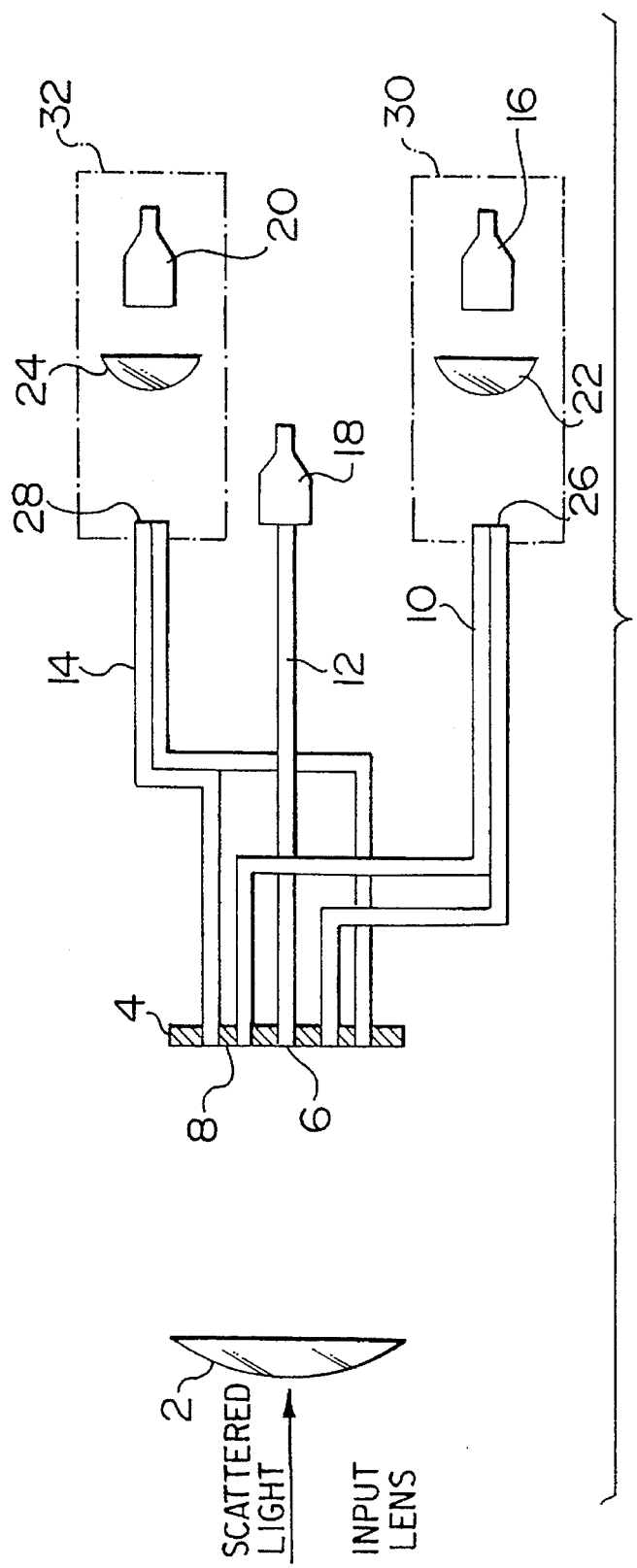
FIG. 1 is a diagrammatic representation of apparatus according to the embodiment.
Figure 2:
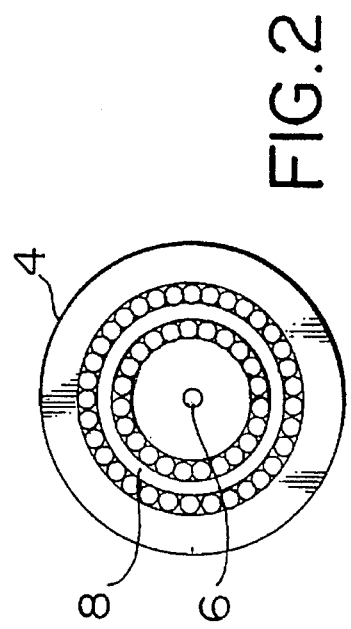
FIG. 2 is a cross-sectional representation of a bundle of optical fibers in FIG. 1.

Referring to FIG. 1, scattered light is incident on an input lens 2 which collects the scattered light and focuses it on the rings of optical fibers in a bundle 4. A central circle 6 collects the light at the focus of the primary input lens 2. This is shown in FIGS. 1 and 2 as a central disk of fibers. Light absorbing spaces, such as 8, are provided in between the rings and these also serve as a retaining structure for the fiber rings. The numerical aperture of the fibers should be chosen to match the small f-number of the input lens, otherwise some collected light will be lost from the apparatus.

Referring to the cross-sectional view of the bundle in FIG. 2, it will be seen that the groups of fibers are arranged in rings. Each ring of fibers forms a group 10, 12 or 14 which is brought out to a respective detector 16, 18 or 20. If the group size is smaller than the respective detector, then the end of the group can be simply fixed to the detector front face by any suitable means, as shown for detector 18. Care must also be used in order that the light emitted in the numerical aperture of the fibers does not overspill the detector active area and be lost to the apparatus. If the group size exceeds the detector size, then a short focal-length lens, aspheric in shape if need be, must be used to project the image of the fiber group onto the detector and reduce the image size to the size of the active area of the detector. Such a short focal-length lens is shown at 22 and 24.

To reduce the possibility of spurious scattering from the apparatus, the ends 26 and 28, lens 22 or 24 and adjacent respective detector 16 or 20 are held in place in a respective container 30 or 32. Each container 30 and 32 is sealed against contamination by dust and other aerosols. Assembly of these containers should be done, if possible, in a clean-room environment.

The fiber core to clad diameter ratio should be as large as possible to ensure maximum light throughput in the fiber. The overall fiber size should be small enough so that the area of the respective scattering ring is filled uniformly. The required uniformity depends on the gradient of the scattering phase function. The phase function should not vary by more than 30% over an angular difference corresponding to the diameter of a single fiber.

For convenience in the above description, the composite assembly of fibers has been referred to as a bundle whereas each ring of fibers is identified as a group. In the art, each ring of fibers is sometimes referred to as a bundle. The composite assembly of rings may then be referred to as a cable.

It will be apparent that in the described embodiment, the use of fiber optic groups allows one to minimize the number of optical services in the received optics of transmissometers and scattering meters. Furthermore, these optical surfaces can be cleaned once during the assembly of the apparatus and then sealed against any further contamination by dust or aerosols. The same method also allows the use of physically separate detectors for each scattering or transmission channel. This substantially prevents what is known in the art as electrical cross-talk from occurring. The susceptibility to parasitic scattering is reduced whilst the groups facilitate a greater flexibility in packaging the apparatus and ease considerably the optical alignment problem. The apparatus is also inherently more rugged and reliable.

Furthermore, the fiber groups permit the use of separate detectors for the transmitted channel and each of the scattering channels. Each detector can thus be optimized separately in terms of signal to noise or speed of response. The detectors are not subject to the problem of cross-talk. A signal from one channel cannot influence the other channels to a great extent.

The optical apparatus has been described as being for transmissometers and scattering meters. It will be understood that the invention is not limited thereto but could be used in any optical apparatus that requires rings of detectors. One such apparatus is the multiple field-of-view lidar system.

It will be readily apparent to a person skilled in the art that a number of variations and modifications can be made without departing from the true spirit of the invention which will now be pointed out in the appended claims.

I claim:

1. Optical apparatus, comprising:

a) a lens which receives scattered light;

b) an optical fiber bundle comprising a central optical fiber and at least one ring of optical fibers therearound, each optical fiber having a first end and a second end, wherein a first end of each of said central optical fiber and first ends of said at least one ring of optical fibers are positioned to receive light passing through said lens, said central optical fiber collecting light at the focus of said lens, the numerical aperture of the fibers being chosen to match the f/number of said lens, and the fiber core to clad diameter of each fiber being selected large enough to ensure maximum light throughput;

c) a plurality of light detectors, wherein each light detector of said plurality of light detectors is positioned to receive light from one of said second end of said central optical fiber and said second ends of said at least one ring of optical fibers; and d) each of said plurality of light detectors having a respective active area, and each respective second end of said central optical fiber and said at least one ring of optical fibers having a respective image size and where a respective light detector of said plurality of light detectors receives light from a second end having an image size larger than said active area, a short focal-length lens being provided between said second end and its respective light detector, substantially all the light from a given ring being collected on to a respective detector, the fiber exit plane being imaged on to the plane of the respective detector with appropriate de-magnification.

2. Optical apparatus according to claim 1, wherein:

each short focal-length lens, its associated optical fiber second end, and respective detector are held in a respective container which is sealed against contamination by dust.

* * * * *